United States Patent [19]

Haedt

[11] Patent Number: 5,439,450
[45] Date of Patent: Aug. 8, 1995

[54] METHOD OF DELIVERING A BLOOD SAMPLE TO AN EVACUATED RECEPTACLE

[75] Inventor: Lori E. Haedt, Marietta, Ga.

[73] Assignee: Becton, Dickinson and Company, Franklin Lakes, N.J.

[21] Appl. No.: 276,390

[22] Filed: Jul. 18, 1994

[51] Int. Cl.⁶ .............................................. A61M 5/32
[52] U.S. Cl. .................................... 604/198; 128/760
[58] Field of Search .................... 128/760, 763–766, 128/770; 604/192, 196–199

[56] References Cited

U.S. PATENT DOCUMENTS

| | | | |
|---|---|---|---|
| 4,874,383 | 10/1989 | McNaughton | 604/198 |
| 5,147,303 | 9/1992 | Martin | 604/198 |
| 5,169,392 | 12/1992 | Ranford et al. | 604/198 |
| 5,242,401 | 9/1993 | Colsky | 604/198 |
| 5,312,370 | 5/1994 | Talonn et al. | 604/198 |

Primary Examiner—Max Hindenburg
Attorney, Agent, or Firm—John L. Voellmicke

[57] ABSTRACT

A method of delivering a blood sample to an evacuated receptacle having a pierceable stopper and a cavity at a subatmospheric pressure, comprising the steps of:
a) providing a syringe comprising a barrel having an open proximal end, a distal end and a chamber for retaining fluid, a needle cannula having a sharp distal end and a lumen therethrough connected to the distal end, a safety shield having an open distal end and a cap having an aperture removably connected thereto, the shield slidably mounted over the barrel for telescoping movement from a proximal position where the needle cannula projects through the aperture to a distal position where the shield protectively surrounds the needle cannula, a piston inside the barrel connected to a rigid elongate plunger rod;
b) piercing a blood vessel with the needle and drawing blood from the vessel into the chamber by manipulating the plunger rod,
c) withdrawing the needle from the vessel;
d) moving the shield to the distal needle protecting position;
e) removing the cap from the shield;
f) inserting evacuated receptacle, stopper first, into the shield until the sharp distal end of the needle cannula pierces stopper and enters the cavity,
g) allowing blood to flow from the syringe chamber through the lumen into the cavity of the receptacle; and
h) removing the receptacle from the safety shield when the desired amount of blood has entered the cavity of the receptacle from the chamber.

9 Claims, 7 Drawing Sheets

METHOD OF DELIVERING A BLOOD SAMPLE TO AN EVACUATED RECEPTACLE

FIELD OF THE INVENTION

The subject invention relates to shielded safety syringes and a method of using such syringes for delivering a blood sample to an evacuated receptacle.

DESCRIPTION OF RELATED INFORMATION

The most common method of withdrawing blood from a mammalian blood vessel, such as a vein or artery of a patient, is by piercing the blood vessel with one end of a double-ended needle cannula. The sharp end of the needle cannula which has not pierced the blood vessel is caused to pierce the pierceable stopper of an evacuated receptacle. When fluid communication is established between the evacuated receptacle and the blood vessel, blood will flow into the cavity of the evacuated receptacle which is initially at a subatmospheric pressure. Also, hypodermic syringes are used to withdraw blood from a vein or artery of a patient. A hypodermic syringe is preferred for withdrawing blood when the patient has weak veins that may collapse under the forces associated with withdrawing the blood directly into an evacuated receptacle. Also, the syringe is in a convenient blood collection device because the collected blood can be easily distributed to several different receptacles or test slides for various diagnostic procedures.

Blood is transferred from a hypodermic syringe to an evacuated receptacle by piercing the pierceable stopper of the receptacle with the needle on the blood filled syringe, and allowing the pressure differential between the evacuated receptacle and the atmosphere to drive the syringe piston and the blood into the receptacle. This method has a drawback in that the technician or medical professional delivering the blood sample to the evacuated receptacle must be careful not to stick herself with the sharpened needle cannula on the syringe which has previously been in the patient's vein. Such a stick could transfer a disease from the patient to the medical technician.

SUMMARY OF THE INVENTION

The present invention includes a method of delivering a blood sample to an evacuated receptacle having a closed end, an open end, a cylindrical side wall therebetween defining a cavity and a pierceable stopper occluding the open end of the receptacle. The cavity is at a subatmospheric pressure. The steps of the method comprise:
  a) providing a syringe assembly comprising a syringe barrel having an open proximal end, a distal end and a, side wall therebetween defining a chamber for retaining fluid, a needle cannula having a sharp distal end and a lumen therethrough connected to the distal end of the syringe barrel so that the lumen is in fluid communication with the chamber, a cylindrical safety shield having an open distal end and an open proximal end and a cap removably connected to the distal end of the safety shield, the cap including an end wall having an aperture smaller than the inside diameter of the open distal end of the shield and smaller than the outside diameter of the receptive stopper for limiting access to the open distal end of the shield, the safety shield is slidably mounted over the syringe barrel for telescoping movement from a proximal position where the needle cannula projects through the aperture of the cap to a distal position where the safety shield surrounds the needle cannula, a piston is in fluid-tight slidable engagement inside the barrel and connected to a rigid elongate plunger rod which extends proximally through the open end of the barrel;
  b) piercing a mammalian blood vessel with the sharp distal end of the needle and drawing blood from the blood vessel into the chamber of the syringe barrel by manipulating the plunger rod;
  c) withdrawing the needle cannula from the blood vessel;
  d) moving the safety shield to the distal needle protecting position;
  e) removing the cap from the distal end of the safety shield;
  f) inserting an evacuated receptacle, stopper first, into the safety shield until the sharp distal end of the needle cannula pierces the stopper and enters the cavity of the receptacle;
  g) allowing blood to flow from the syringe barrel chamber through the needle cannula lumen and into the cavity of the receptacle; and
  h) removing the receptacle from the safety shield when the desired amount of blood has entered the cavity from the chamber.

DETAILED DESCRIPTION

While this invention is satisfied by embodiments in many different forms, there are shown in the drawings and will herein be described in detail, preferred embodiments of the invention with the understanding that the present disclosure is to be considered exemplary of the principles of the invention and is not intended to limit the invention to the embodiments illustrated. The scope of the invention will be measured by the appended claims and their equivalents.

Adverting to FIGS. 1-10, the present invention relates to a method for delivering a blood sample to an evacuated receptacle. Evacuated blood collection tubes or receptacles are well known in the art and are commercially available. The VACUTAINER Brand Blood Collection Tube manufactured by Beeton, Dickinson and Company is the most widely used evacuated blood collection tube. Evacuated receptacles are available with a wide variety of additives such as coagulants, anticoagulants, various compounds to facilitate diagnostic testing, and inert gel materials which provide a barrier to separate the serum after centrifugation of the blood sample. Evacuated receptacles also are available with liquid culture growth medium therein. A typical evacuated receptacle 20 includes a closed end 21 an opposed open end 22, a cylindrical side wall 23 therebetween defining a cavity 25, and a pierceable stopper 26 occluding the open end. Evacuated receptacles may be made with glass or plastic side wall and end portions. The pierceable stopper is made of rubber. Evacuated receptacles are assembled in subatmospheric conditions so that the cavity is evacuated and at a subatmospheric pressure. Receptacles containing culture medium can have a long cylindrical neck portion which holds the stopper and a larger diameter base portion for holding most of the liquid culture medium.

The method of the present invention uses a syringe assembly 28 comprising a syringe barrel 29 having an open proximal end 31 a distal end 32 and a side wall 33 therebetween defining a chamber 34 for retaining fluid. A needle cannula 37 having a sharp distal end 38 and a lumen therethrough is connected to distal end 32 of the syringe barrel so that the lumen is in fluid communication with chamber 34 of the syringe barrel.

It is within the purview of the present invention to include a needle cannula which is permanently attached to the syringe barrel such as through the use of mechanical elements and/or adhesives such as epoxy. In this preferred embodiment the needle cannula is attached to a needle hub 39 having an interior conduit 40. Needle cannula 37 is connected to the needle hub so that the lumen of the needle cannula is in fluid communication with interior conduit 40. Interior conduit 40 is frusto-conically shaped to frictionally engage frusto-conically shaped tip 35 on the distal end of the syringe barrel. The distal end of the syringe barrel also includes locking luer-type collar 36 adjacent to and in spaced concentric relationship around tip 35. Luer collar 36 includes an internal thread 41 to enable threaded mounting of the needle hub between the collar and the syringe tip. Accordingly, the needle assembly which includes needle hub 39 and needle cannula 37 is releasably connected to the syringe barrel. The needle assembly is connected to the syringe barrel by rotating the needle assembly so that projections 43 on the needle hub follow internal thread 41 on the locking luer collar to pull the needle hub axially so that the exterior frusto-conically shaped tip 35 frictionally engages frusto-conically shaped interior conduit 40 of the needle hub. The needle assembly may be disconnected from the hub by rotation of the needle assembly in the direction opposite of that required for installation.

Figure 1:
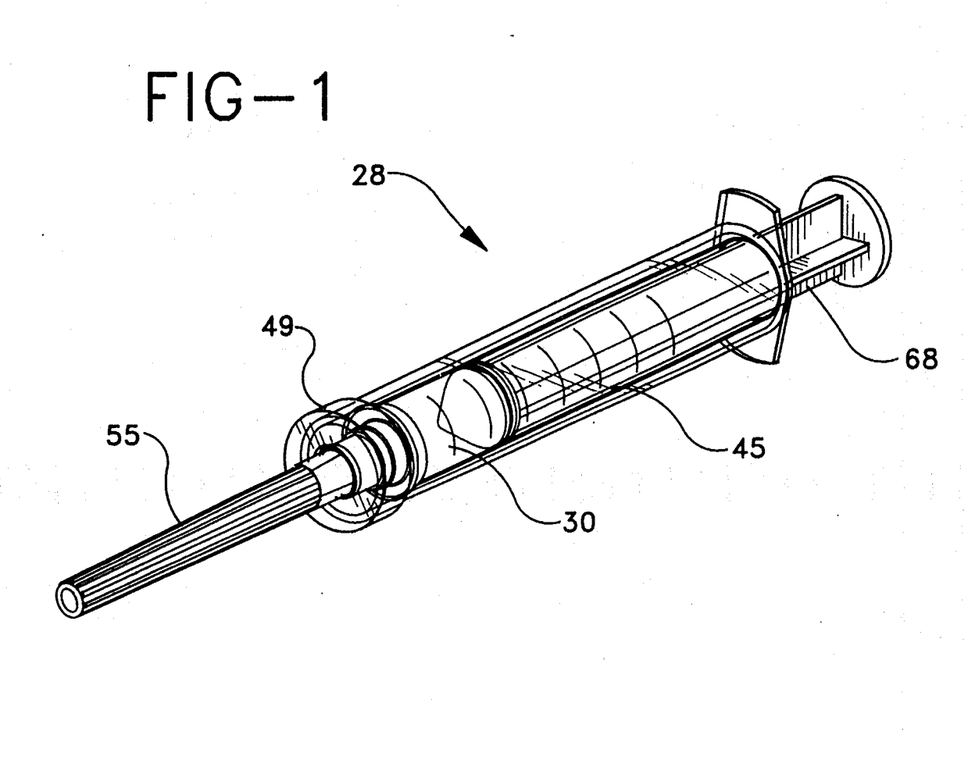
FIG. 1 is a perspective view of a hypodermic syringe having a slidable safety shield.
Figure 2:
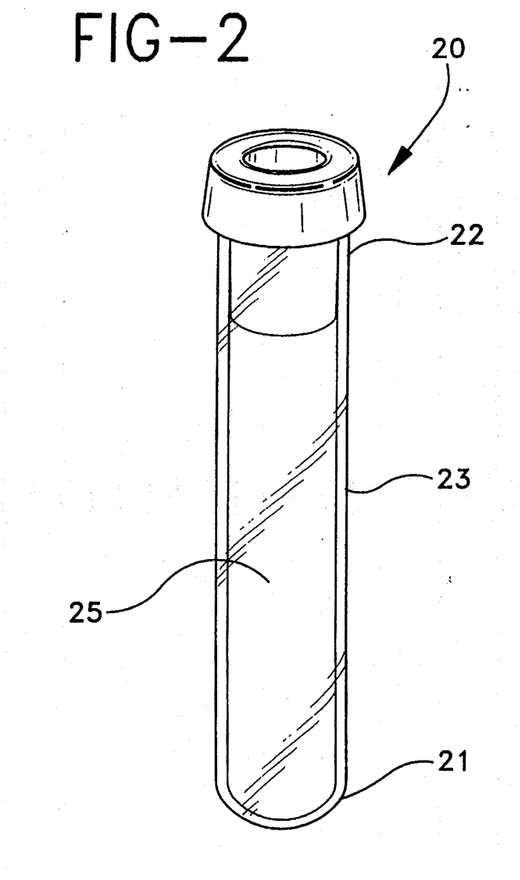
FIG. 2 is a perspective view of an evacuated receptacle having a pierceable stopper.

Syringe assembly 28 includes a cylindrical safety shield 45 having an open distal end 46 and an open proximal end 47. A cap 49 is removably connected to distal end 46 of the safety shield. Cap 49 includes an end wall 50 having aperture 51 therein. The diameter of aperture 51 is less than the inside diameter of safety shield 45 for limiting access to the open distal end of the safety shield to further reduce the probability of accidental needle sticks. The diameter of aperture 51 is also less than the outside diameter of the portion of the evacuated receptacle stopper which is outside of the receptacle. Cap 49 also includes cylindrical side wall 52 preferably having a larger outside diameter than the outside diameter of the safety shield. In the preferred embodiment cylindrical side wall 52 of the cap includes inwardly projecting annular surface 53 which cooperates with outwardly projecting annular surface 48 so that the cap engages the safety shield in a snap-fit type arrangement. Accordingly, the cap can be installed and removed by forces sufficient to overcome the interference between inwardly projecting annular surface 53 on the cap and outwardly projecting annular surface 48 on the safety shield. The syringe as manufactured and delivered preferably contains the cap installed as illustrated in FIGS. 1, 3, 4 and 5. As best illustrated in FIG. 1, a syringe as manufactured preferably contains a rigid removable safety cover 55. This cover frictionally engages the needle hub and is removed and discarded at the time of use either by physically removing the cover from the needle hub or by making the aperture in the cap smaller than the outside diameter of the needle cover so that forward motion of the needle shield dislodges the needle cover from its hub engaging position.

Figure 3:
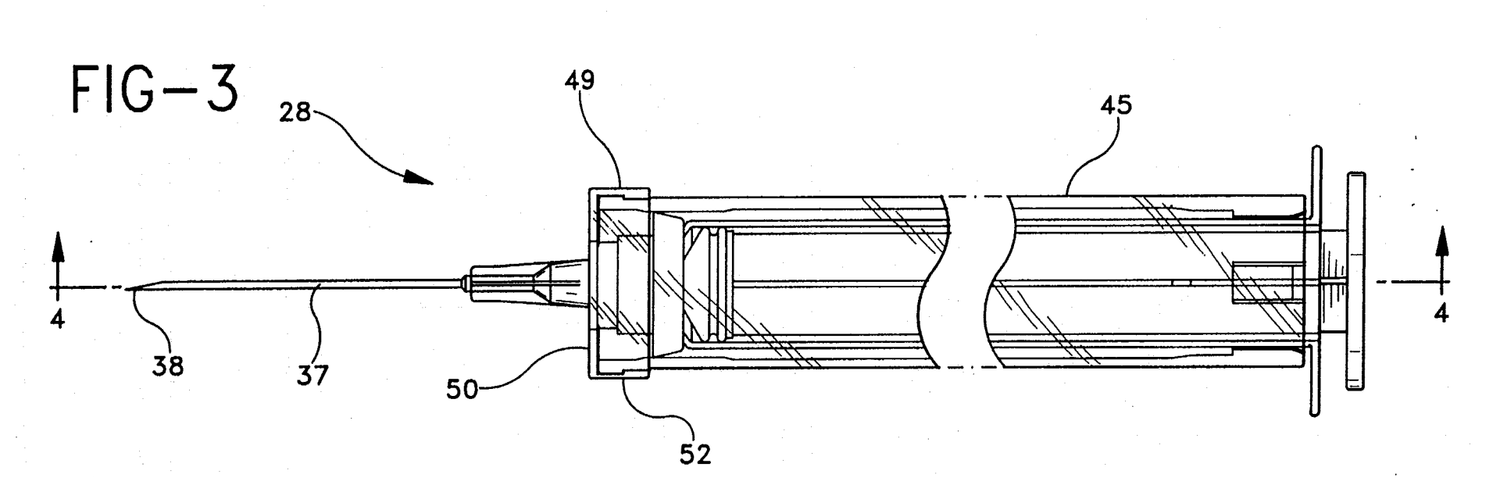
FIG. 3 is a side elevation view of the syringe assembly of FIG. 1 with the needle guard removed.
Figure 4:
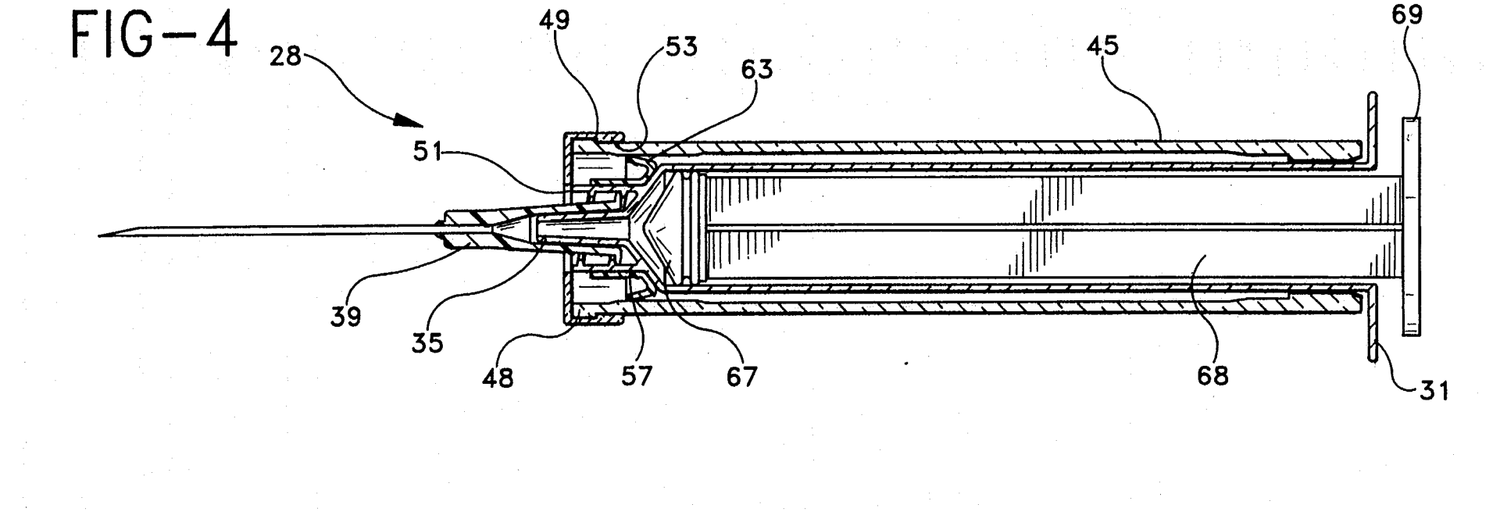
FIG. 4 is a cross-sectional view of the syringe of FIG. 3 taken along line 4—4.
Figure 5:
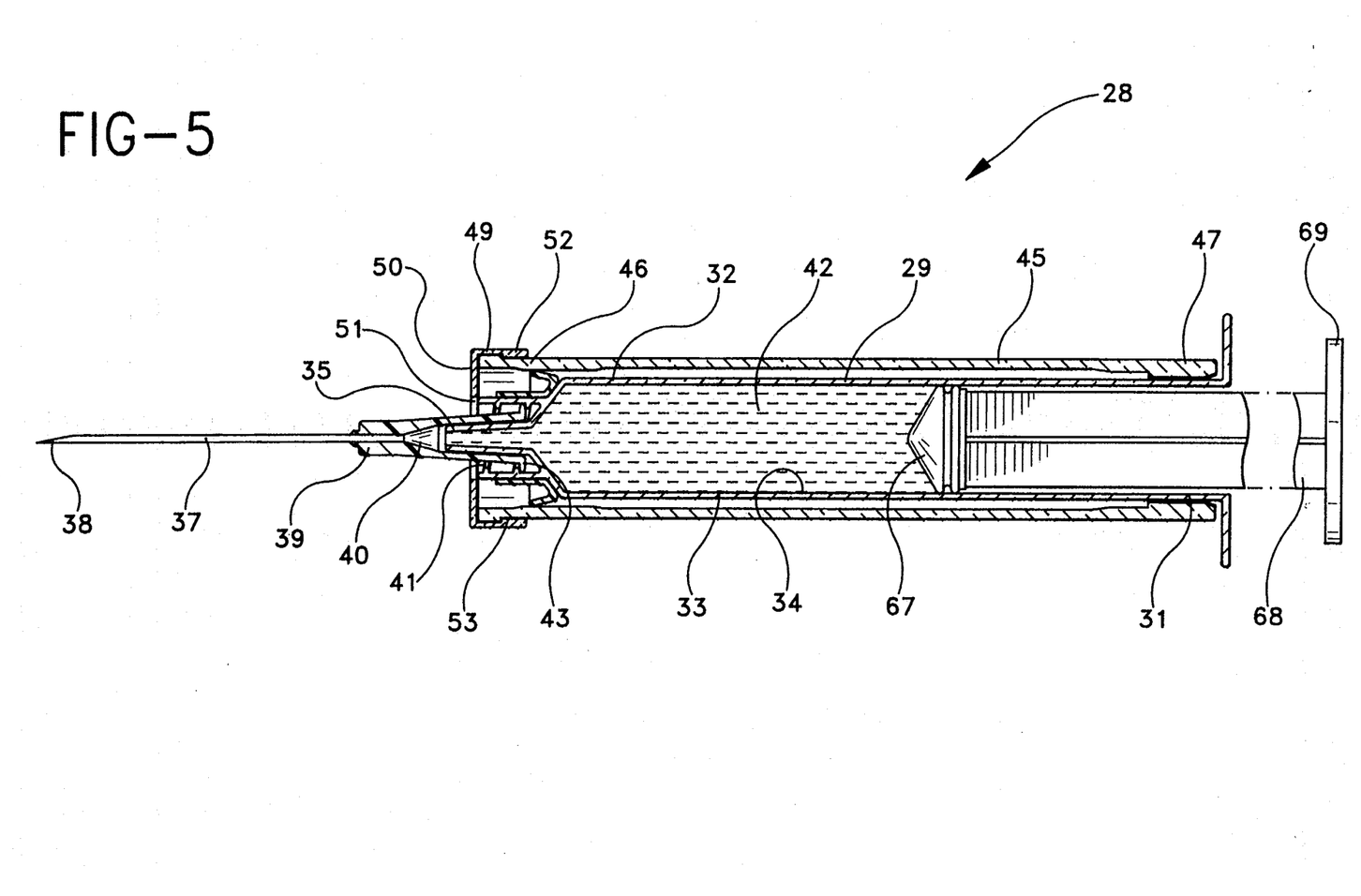
FIG. 5 is a cross-sectional view, similar to FIG. 4, illustrating the syringe assembly containing blood drawn from a patient.
Figure 6:
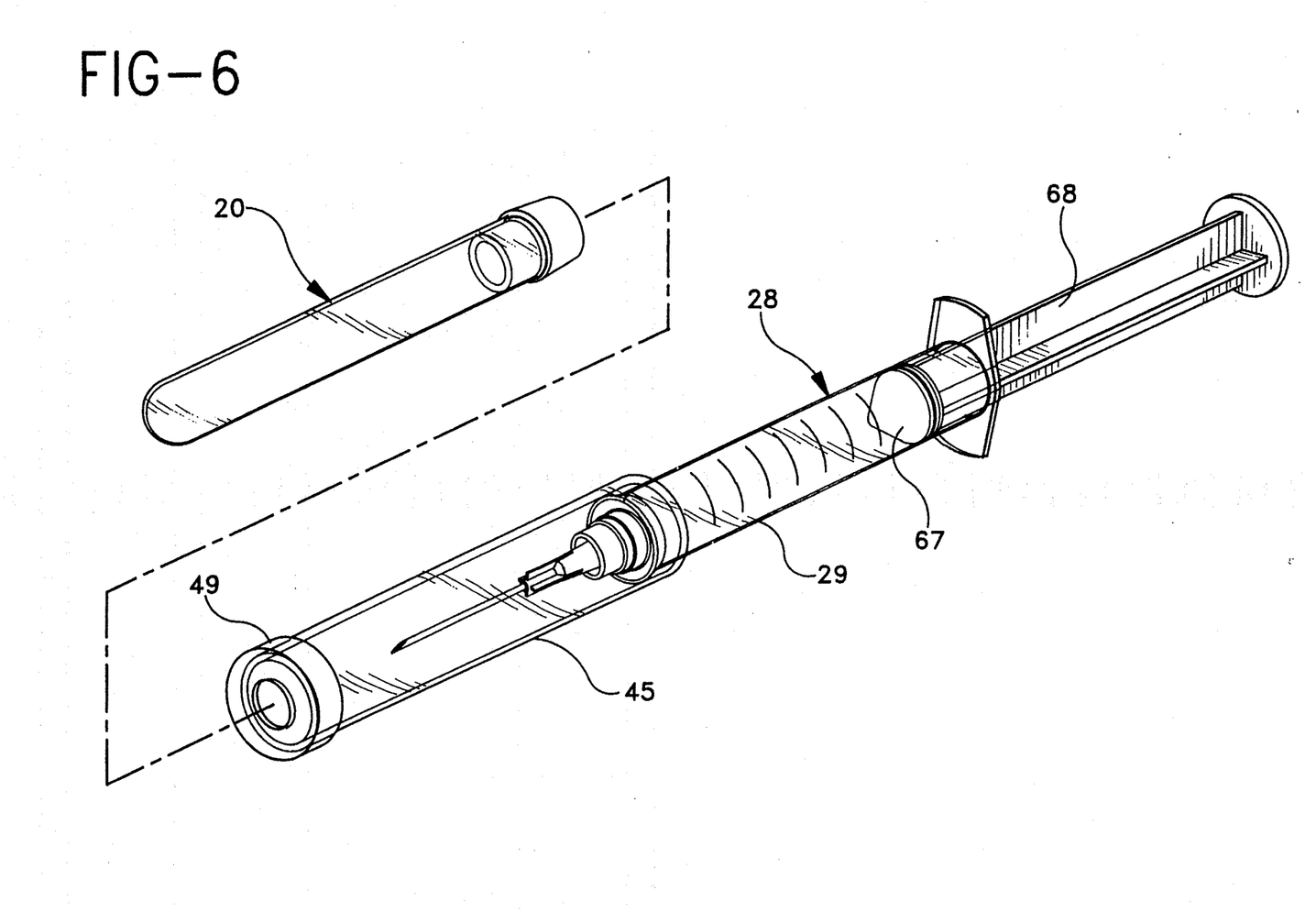
FIG. 6 is an exploded view showing an evacuated receptacle and the syringe of FIG. 5 with its safety shield in a distal needle protecting position.
Figure 8:
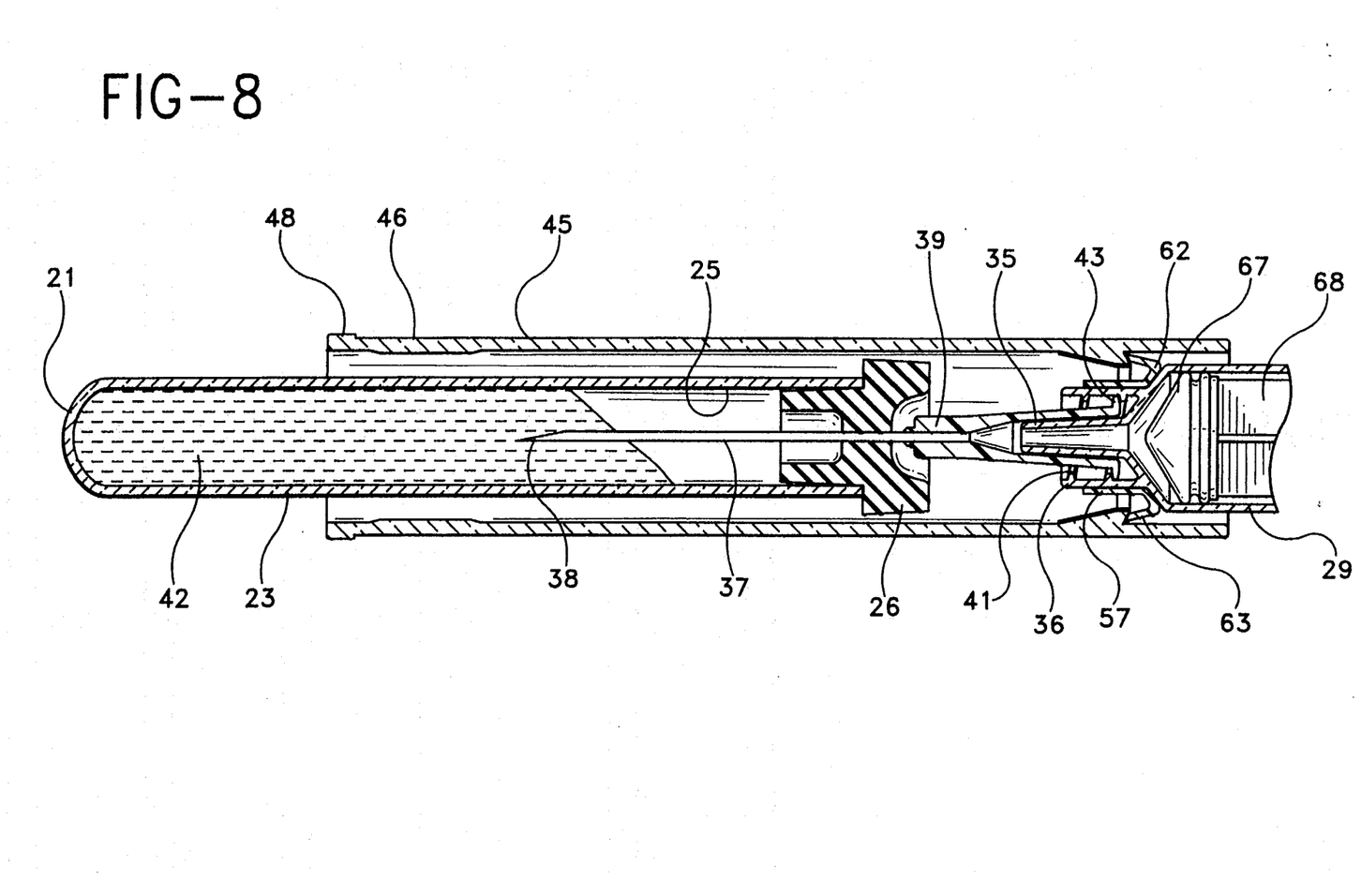
FIG. 8 is a partial cross-sectional view of the syringe assembly and evacuated receptacle of FIG. 7 taken along line 8—8.

Safety shield 45 is slidably mounted over syringe barrel 29 for telescoping movement from a proximal position as best illustrated in FIGS. 3-5, where the needle cannula projects through aperture 51 of cap 49, to a distal position, as best illustrated in FIGS. 6 and 8, where the safety shield protectively surrounds the needle cannula.

Figure 9:
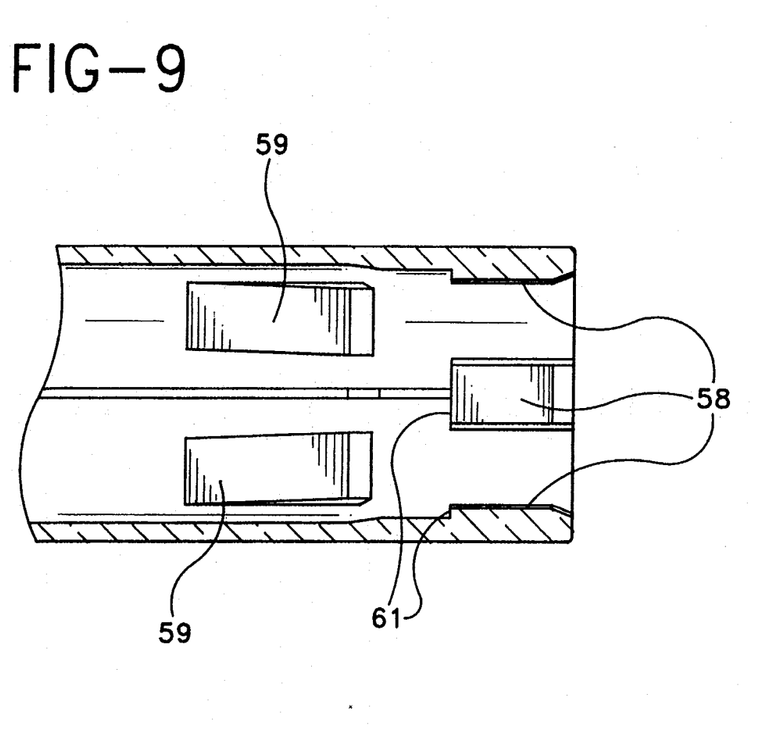
FIG. 9 is a partial cross-sectional view of the safety shield illustrating locking projections for preventing movement of the safety shield after it is in the distal needle protecting position.
Figure 10:
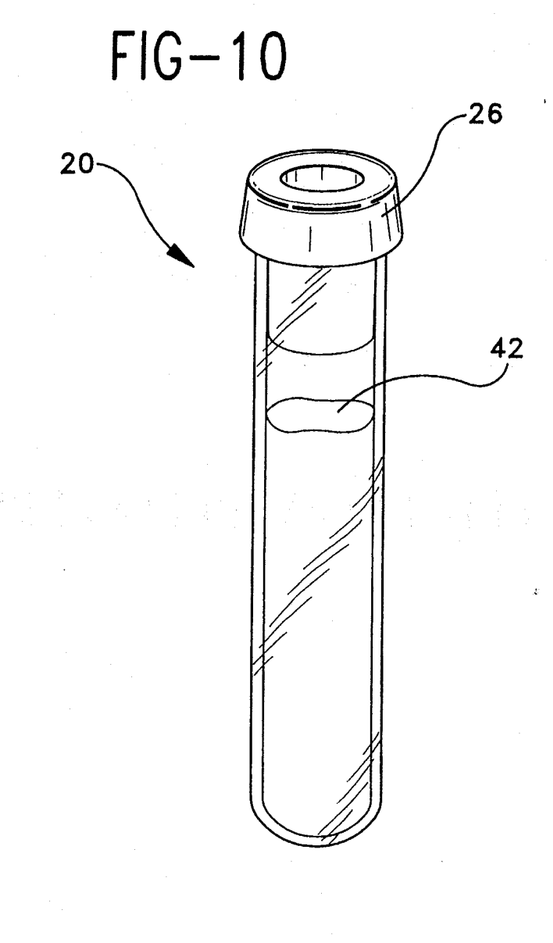
FIG. 10 is an evacuated receptacle containing a blood sample.

In the preferred embodiment, safety shield 45 can be locked in the distal needle protecting position. Locking is achieved through cooperation between collar 57 on the distal end of the syringe barrel and inwardly projecting stop locks 58 and ramped locking teeth 59 at the proximal end of the safety shield. In particular, collar 57 includes solid annular stop wall 62 which includes distally extending frusto-conically shaped projection 63. Collar 57 is fixedly attached to the distal end of the syringe barrel through the use of adhesives or mechanical means. The collar can also be attached to or be an integral part of the needle hub. As the safety shield is telescoped from the proximal position to the distal position, distally extending frusto-conically shaped projection 63 deflects as it passes over the ramped locking teeth and becomes trapped between ramped locking teeth 59 and stop surfaces 61 on stop locks 58. At this position the safety shield cannot be returned to the proximal position.

U.S. Pat. No. 5,169,392 also teaches a syringe assembly having a safety shield, a collar mounted on the distal end of the syringe barrel and inwardly directed projections on the proximal end of the safety shield positioned to cooperate with the collar for releasably holding the safety shield when the shield is in the distal needle protecting position. Specifically, U.S. Pat. No. 5,169,392 teaches a syringe and needle assembly wherein the shield can move back and forth over the barrel of the syringe to alternately expose or shield the needle tip from user contact. The collar and shield structure allows the needle shield to be in the fully extended position and not locked. In order to lock the safety shield in the fully extended position the shield must be rotated with respect to the barrel so that inwardly directed projections or keys on the inside surface of the shield will snap over angled surfaces on the collar and be locked in blind slots so that proximal motion of the sleeve with respect to the barrel will be resisted by surfaces on the keys which abut against squared-off surfaces of the blind slots. Syringes like the syringe taught in U.S. Pat. No. 5,169,392 are suitable for use in and are within the purview of the method of the present invention.

A piston 67 is in fluid-tight slidable engagement inside the syringe barrel. An elongate rigid plunger rod 68 is connected to the piston and extends proximally through open proximal end 31 of the barrel.

The method of the present invention includes providing a syringe assembly of the type having a safety shield and a removable cap such as described or as referred to hereinabove. With the safety shield in the proximal needle exposing position, the sharp distal end of the needle cannula is urged into a mammalian blood vessel such as the vein of a patient until fluid communication is established between the lumen of the needle and the interior of the blood vessel. The user then applies a gentle, proximally directed force on plunger rod 68, through plunger rod flange 69 to draw blood from the blood vessel into chamber 34 of the syringe barrel so that the chamber contains the desired quantity of blood, indicated by numeral 42. To determine the volume of blood in the syringe barrel, volume measuring indicia printed on the outside diameter of the cylindrical side wall, as best illustrated in FIG. 1, are provided. When the desired amount of blood is obtained the needle cannula is withdrawn from the blood vessel.

The user then telescopes safety shield 45 to the distal needle protecting position. It is preferred that when the safety shield is in the distal needle protecting position it is locked in the distal position and incapable of returning to a needle exposing position through structure involving cooperating structure on the barrel and the inside of the safety shield. The preferred embodiment includes a collar and inwardly directed projections in the proximal end of the safety shield. The projections in the safety shield cooperate with the collar when the safety shield is in the distal needle protecting position to lock the shield in the distal needle protecting position for preventing exposure of the sharpened distal tip of the needle cannula. Other cooperating structure between a collar on the syringe barrel and projections on the inside of a safety shield, such as that taught in U.S. Pat. No. 5,169,392, allows the safety shield to be releasably held in the distal needle protecting position. Both structures are within the purview of the present invention.

Figure 7:
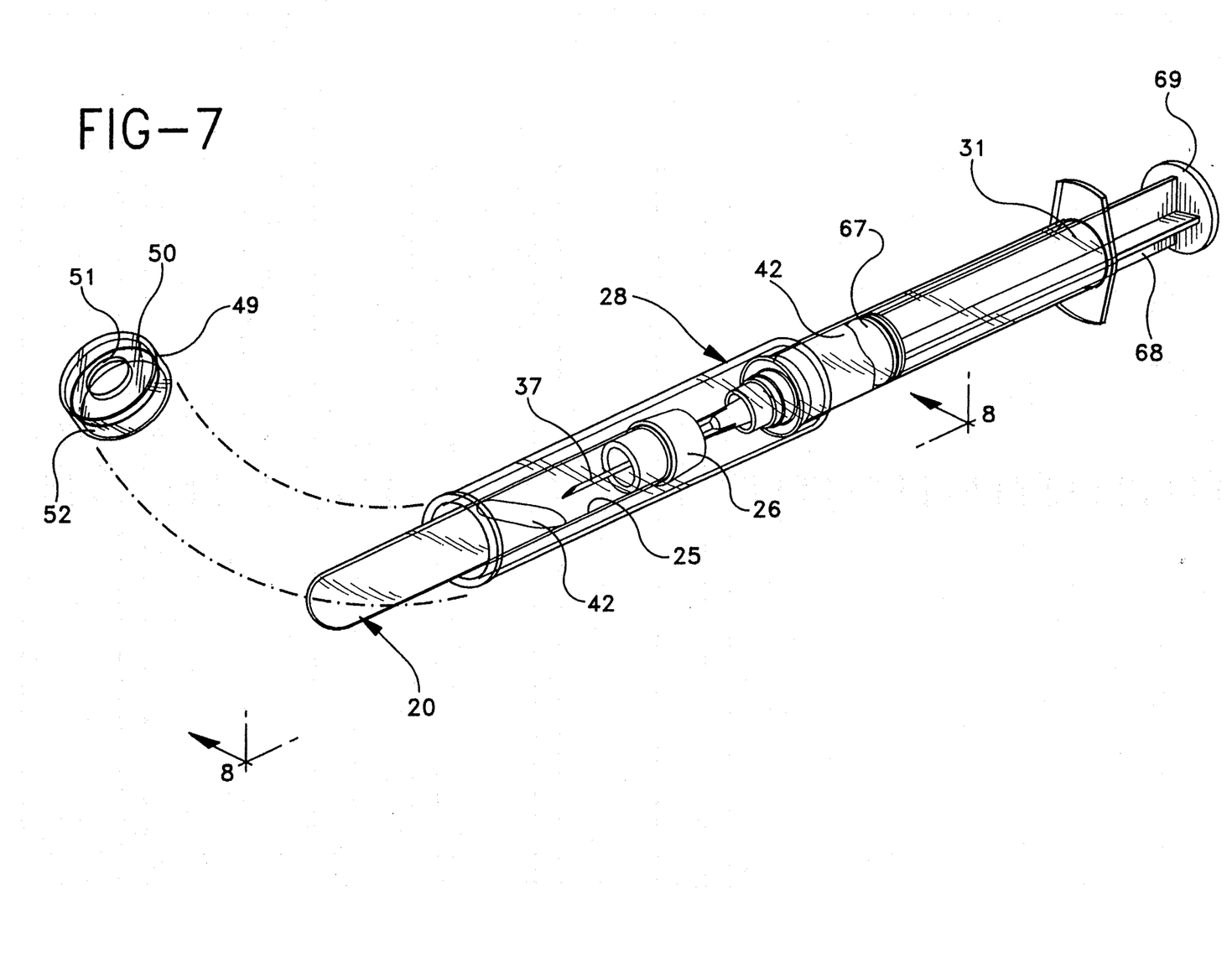
FIG. 7 is an exploded view illustrating the cap removed from the safety shield and the evacuated receptacle inserted in the safety shield with the needle cannula piercing the pierceable stopper and blood entering the evacuated receptacle.

With the safety shield in the distal position, the user then removes cap 49, as illustrated in FIG. 7 so that the opening in the distal end of the safety shield is now large enough to accept an evacuated receptacle. The user then inserts evacuated receptacle 20, with stopper 26 first, into the safety shield until sharp distal end 38 of the needle cannula pierces pierceable stopper 26 of the evacuated receptacle and enters cavity 25 of the tube. The subatmospheric pressure in the tube should be sufficient to allow the atmospheric pressure to move the plunger rod distally and allow blood to enter the evacuated receptacle. Accordingly, in most situations, the user will observe the movement of the plunger rod and will allow blood to flow from the syringe chamber through the lumen of the needle cannula into the cavity of the tube until the desired amount of blood has entered the cavity from the chamber in the barrel. Although not preferred, the plunger rod 69 may be manipulated to urge blood from the syringe barrel into the receptacle. When the desired amount of blood has entered the receptacle, the user removes the receptacle from the safety shield.

The syringe assembly containing blood, may then be used to provide blood to one or more additional evacuated receptacles by following the same steps as described hereinabove. Specifically, the user provides a second evacuated receptacle and inserts this receptacle, stopper first, into the safety shield until the sharp distal end of the needle cannula pierces the stopper and enters the cavity. The user then allows blood to flow from the syringe chamber through the lumen of the needle cannula into the cavity of the second evacuated receptacle. When the desired amount of blood has entered the second receptacle it is removed from the safety shield of the syringe assembly.

In some instances it is desired to culture the patient's blood to determine the existence of bacteria using culture medium containing receptacles described above. When testing for bacteria it is often desirable to disconnect the needle cannula from the syringe barrel after the needle cannula is withdrawn from the patient's blood vessel. This needle cannula is discarded because it may contain bacteria which came from the surface of the patient's skin and not from the patient's blood. At this point, the user provides a second needle cannula and connects the second needle cannula to the distal end of the syringe barrel. The safety shield may now be telescoped to the distal needle protecting position and the additional steps, described hereinabove, may be practiced. It is preferred that the syringe barrel have a chamber volume of at least 10 cc.

The present invention provides a method for withdrawing blood from a patient using a hypodermic syringe and delivering the blood to one or more evacuated receptacles or other test devices using a hypodermic syringe having a telescoping safety shield with a removable cap which will reduce the possibility of accidental needle sticks during this procedure.

What is claimed is:

1. A method of delivering a blood sample to an evacuated receptacle having a closed end, an opposed open end, a cylindrical side wall therebetween defining a cavity, and a pierceable stopper occluding the open end, the cavity being at a subatmospheric pressure, comprising the steps of:

a) providing a syringe assembly comprising a syringe barrel having an open proximal end, a distal end and a side wall therebetween defining a chamber for retaining fluid, a needle cannula having a sharp distal end and a lumen therethrough connected to said distal end so that said lumen is in fluid communication with said chamber, a cylindrical safety shield having an open distal end and an open proximal end, a cap removably connected to said distal end of said safety shield, said cap having an aperture smaller than the inside diameter of said open distal end of said shield for limiting access to said open distal end of said shield, said safety shield slidably mounted over said syringe barrel for telescoping movement from a proximal position where said needle cannula projects through said aperture to a distal position where said safety shield protectively surrounds said needle cannula, a piston in fluid-tight slidable engagement inside said barrel, a rigid elongate plunger rod connected to said piston and extending proximally through said open proximal end of said barrel;

b) piercing a mammalian blood vessel with said sharp distal end of said needle and drawing blood from said blood vessel into said chamber by manipulating said plunger rod;

c) withdrawing said needle from said blood vessel;

d) moving said safety shield to said distal needle protecting position;

e) removing said cap from said distal end of said safety shield;

f) inserting said evacuated receptacle, stopper first, into said safety shield until said sharp distal end of said needle cannula pierces said stopper and enters said cavity of said receptacle;

g) allowing blood to flow from said syringe chamber through said lumen into said cavity of said receptacle; and h) removing said receptacle from said safety shield when the desired amount of blood has entered said cavity of said receptacle from said chamber.

2. The method of claim 1 further comprising the additional steps of:

i) providing a second evacuated receptacle having a closed end, an opposed open end, a cylindrical side wall therebetween defining a cavity, and a pierceable stopper occluding the open end, the cavity being at subatmospheric pressure;

j) inserting said second evacuated receptacle, stopper first, into said safety shield until said sharp distal end of said needle cannula pierces said stopper and enters said cavity;

k) allowing blood to flow from said syringe chamber through said lumen into said cavity of said second evacuated receptacle; and l) removing said second receptacle from said safety shield when the desired amount of blood has entered said cavity from said chamber.

3. The method of claim 1 wherein said needle cannula is removably connected to said distal end of said syringe barrel.

4. The method of claim 3 including the additional steps immediately after withdrawing said needle from said blood vessel, said steps comprising:

c1) disconnecting said needle cannula from said barrel;

c2) providing a second needle cannula; and c3) connecting said second needle cannula to said distal end of said syringe barrel.

5. The method of claim 1 wherein said syringe barrel includes a collar connected to said distal end of said syringe barrel and inwardly directed projections in said proximal end of said safety shield positioned to cooperate with said collar when said safety shield is in said distal needle protecting position to lock said shield in said distal needle protecting position for preventing re-exposure of the sharpened distal tip of the needle cannula.

6. The method of claim 1 wherein said syringe barrel includes a collar connected to said distal end of said syringe barrel and inwardly directed projections in said proximal end of said safety shield positioned to cooperate with said collar for releasably holding said shield when said safety shield is in said distal needle protecting position.

7. The method of claim 1 wherein said cap includes a cylindrically shaped side wall having an outside diameter larger than the outside diameter of said safety shield.

8. The method of claim 1 wherein said chamber of said syringe barrel has a fluid containing volume of at least 10 cc.

9. The method of claim 7 wherein said cylindrical side wall of said cap engages the outside diameter of said safety shield.

* * * * *